United States Patent [19]

Nakagawa et al.

[11] Patent Number: 5,299,450
[45] Date of Patent: Apr. 5, 1994

[54] METHOD FOR EVALUATING PERFORMANCE OF ALUMINUM ALLOY WIRING FILM

[75] Inventors: Toshiaki Nakagawa, Tenri; Hisakazu Miyatake, Nara, both of Japan

[73] Assignee: Sharp Kabushiki Kaisha, Osaka, Japan

[21] Appl. No.: 871,757

[22] Filed: Apr. 21, 1992

[30] Foreign Application Priority Data

Apr. 24, 1991 [JP] Japan .................. 3-094353

[51] Int. Cl.$^5$ ...................... G01N 3/40; G01N 33/20
[52] U.S. Cl. ............................. 73/78; 73/866
[58] Field of Search ............ 73/78, 79, 81, 82, 83, 73/85, 866, 150 R, 150 A

[56] References Cited

U.S. PATENT DOCUMENTS

| | | |
|---|---|---|
| 2,564,519 | 8/1951 | Bergsman .............. 73/78 UX |
| 2,568,713 | 9/1951 | Brenner ................ 73/866 X |
| 2,735,304 | 2/1956 | Berwick, Jr. ............. 73/866 |
| 3,003,352 | 10/1961 | Ziegler et al. ............ 73/78 X |
| 4,419,885 | 12/1983 | Holmstrom et al. ......... 73/78 |
| 4,791,807 | 12/1988 | Oeschle ................. 73/78 |
| 5,051,373 | 9/1991 | Yamada et al. ......... 364/490 X |
| 5,175,115 | 12/1992 | Abe et al. ............. 73/766 X |

FOREIGN PATENT DOCUMENTS

| | | | |
|---|---|---|---|
| 2735340 | 2/1979 | Fed. Rep. of Germany ......... 73/78 |
| 91237 | 5/1985 | Japan ......................... 73/78 |
| 132145 | 6/1987 | Japan ......................... 73/78 |
| 311734 | 12/1988 | Japan ......................... 73/866 |
| 1359715 | 12/1987 | U.S.S.R. ...................... 73/78 |

OTHER PUBLICATIONS

Ind. Lab. (USA) vol. 45, No. 10, pp. 1184–1185 (Oct. 1979) pub. Apr. 1980 "Measurement of the Microhardness of Polymer Materials"; A. I. Barkan et al.

RCA Technical Notes: TN No. 1368: Mailed Jun. 25, 1985 "Device for Testing Brittle Coating on a Wire"; S. W. Haun; 2 pages.

*Primary Examiner*—Tom Noland
*Attorney, Agent, or Firm*—Nixon & Vanderhye

[57] ABSTRACT

A method for evaluating performance of an aluminum alloy wiring film includes the steps of forming a first aluminum alloy film on a substrate, forming a second aluminum alloy film on another substrate, measuring hardness of the both films, and evaluating the superiority of stressmigration of the aluminum alloy films by comparison between the films in hardness.

8 Claims, 2 Drawing Sheets ial No. 5,299,450

METHOD FOR EVALUATING PERFORMANCE OF ALUMINUM ALLOY WIRING FILM

BACKGROUND OF THE INVENTION

1. Field of the Invention

The present invention relates to a method for evaluating performance of an aluminum alloy wiring film and more particularly, to a method for evaluating stressmigration tolerance of a wiring film in an integrated circuit element.

2. Description of the Related Art

The stressmigration of the metal wiring film in the integrated circuit element is determined by stress of a protective film on the metal wiring film and critical stress of the wiring film. According to a conventional method for evaluating performance of a metal wiring film, a protective film is laminated on the metal wiring film to be evaluated and aged for a long time at approximately 150° C. and then a void is observed by a microscope or an existence of burnout is confirmed by measuring resistance of the wiring film.

However, the conventional evaluating method requires a lot of evaluating samples and a long time, which is a problem.

SUMMARY OF THE INVENTION

The present invention provides a method for evaluating performance of an aluminum alloy wiring film, which method comprises the steps of forming a first aluminum alloy film on a substrate, forming a second aluminum alloy film on another substrate, measuring surface hardness of both films, and evaluating the superiority of stressmigration tolerance of the aluminum alloy films by comparison between the films in hardness.

Further, the present invention provides a method for evaluating performance of an aluminum alloy wiring film, which method comprises the steps of forming a reference aluminum alloy film having a predetermined thickness on a substrate, forming an aluminum alloy film to be evaluated on another substrate with the same thickness as that of the reference film, measuring surface hardness of the both films, forming a protective film on the evaluated film if its hardness is higher than that of the reference film, and aging it to evaluate stressmigration tolerance of the aluminum alloy film having the protective film.

In addition, the reference film and the film to be evaluated are preferably formed on the substrate by sputtering.

In addition, the substrates preferably have a BPSG film on its surface.

DESCRIPTION OF THE PREFERRED EMBODIMENTS

It is known that there are two following relations between stressmigration tolerance and physical properties of a metal wiring film. That is, (1) The smaller the grain size of the metal wiring film is, the higher the stressmigration tolerance of the metal wiring film is.

(2) The stressmigration tolerance of the metal wiring film becomes high by adding an impurity.

Meanwhile, the relation between the grain size and the hardness of the metal wiring film has been well known by the Hall-Petch relation (referring to E. O. Hall, :Proc. Phys. Soc., B649 (1951), p747 and N. J. Petch, :J. Iron Steel Inst., 173 (1953), p25), that is, $$t_{ys} = t_o + k_y \cdot d^{-\frac{1}{2}}$$

where $t_{ys}$ is the yield strength and $t_o$, $k_y$ are constant and d is the grain size. The yield strength and the hardness have the same dimension as $ML^{-1}$. Therefore, it could be said that the Hall-Petch relation holds between the grain size and the hardness.

In other words, the hardness becomes high in proportion to the reciprocal of the square root of a grain size d. Therefore, it is found that the higher the hardness of the metal film is, the higher the migration tolerance of the metal wiring film is, from the Hall-Petch relation and the relation described in the above (1). In addition, it is also known that the more the impurity is applied to the metal wiring film, the higher the hardness thereof is. Therefore, it follows that the higher the hardness is, the higher the stressmigration tolerance is from the above fact and the relation described in the above (2). More specifically, the stressmigration tolerance of the metal wiring film can be evaluated by measuring its hardness. Therefore, when the hardness of the metal film to be evaluated is lower than that of the reference metal film, the inferiority of the stressmigration of the metal film is evaluated without evaluation by aging, so that the evaluation can be efficiently performed.

I Description of the Present Invention by Experiment

The principle of the present invention will be described in reference to the result of an experiment.

Figure 1:
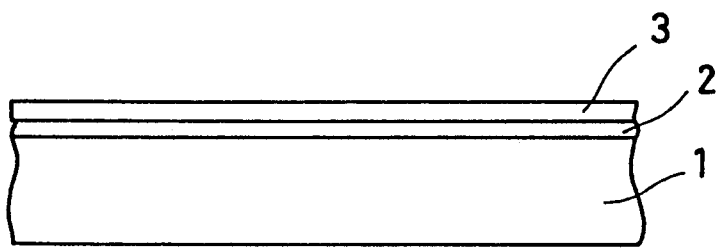
FIG. 1 is a view showing a substrate on which metal films are laminated according to the present invention.

As shown in FIG. 1, a BPSG (Borophosphosilicate glass) film 2 having a thickness of 0.9 μm is formed on a silicon substrate (bare Si wafer) 1 by a CVD method. Then, an Al-Si film having a thickness of 1.1 μm is formed thereon as a metal film 3 by sputtering. Then, in order to obtain samples of the wiring films having different grain sizes, a temperature when the Al-Si film is formed is set at a room temperature, at 150° C. and 300° C. Then, as the metal film 3, samples are formed of an Al-Si-Pd film and an Al-Si-Cu film instead of the Al-Si film in the same manner as above.

Next, the hardness of each of these metal films of samples is measured using a microhardness meter (MHPIB made by Carl Zeiss Foundation).

Then, using a method of boundary-etching (referring to E. G. Solley et al.; Solid State Technology, Japanese, March, 1990, p.31), the particles of the metal film can be embossed on the surface and then its grain size d is found by a scan type electron microscope.

Figure 2:
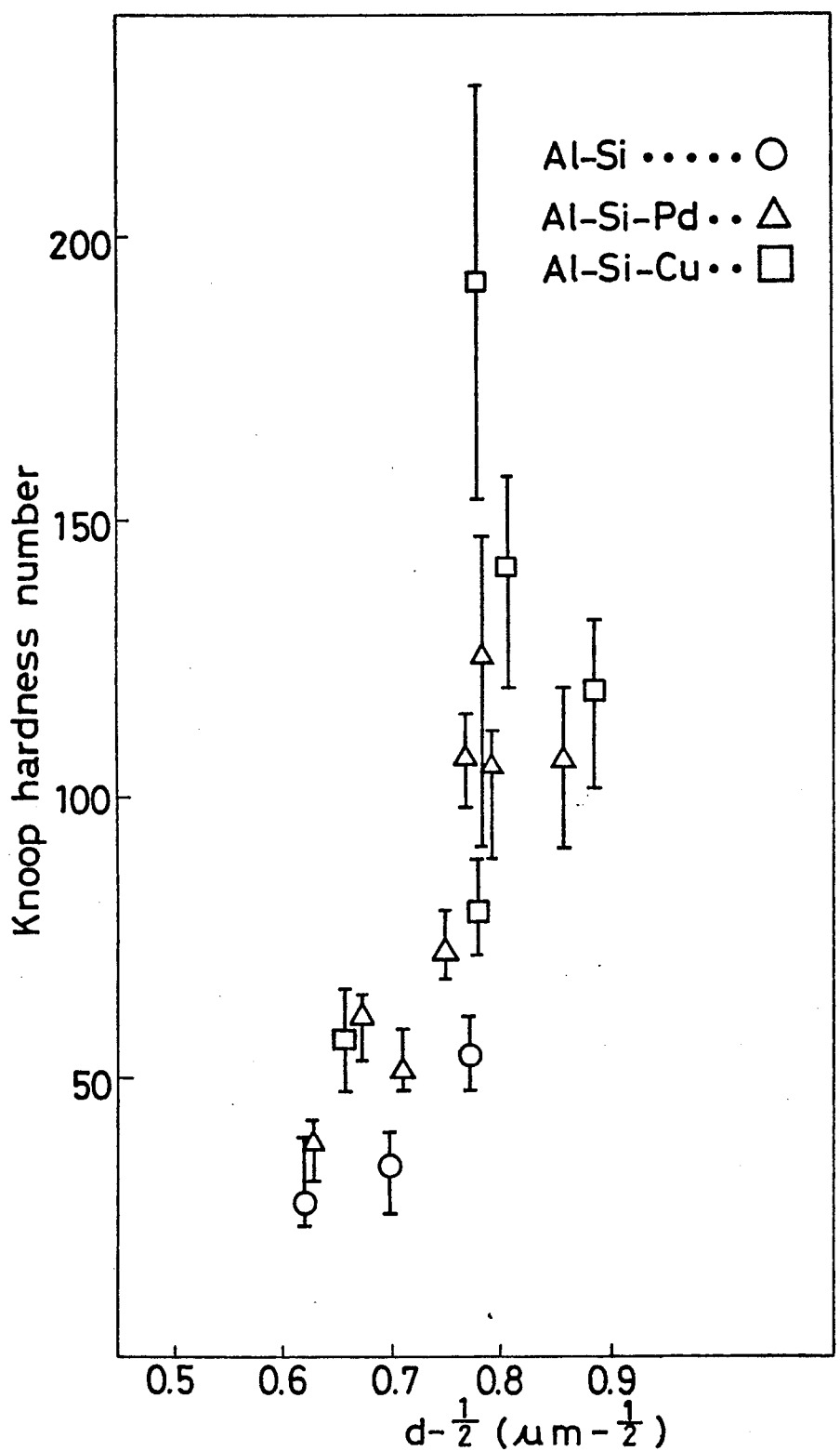
FIG. 2 is a graph showing the relation between a grain size and hardness of the metal film according to the present invention.

An example of the result of measurement of the hardness and the grain size d is shown in FIG. 2. As can be seen from FIG. 2, the larger the grain size is, the lower the hardness is, which is not contradictory to the above Hall-Petch relation.

In addition, it is found that the hardness of the Al-Si-Pd film or the Al-Si-Cu film is higher than that of the Al-Si film and the hardness is increased by adding an impurity.

Figure 3:
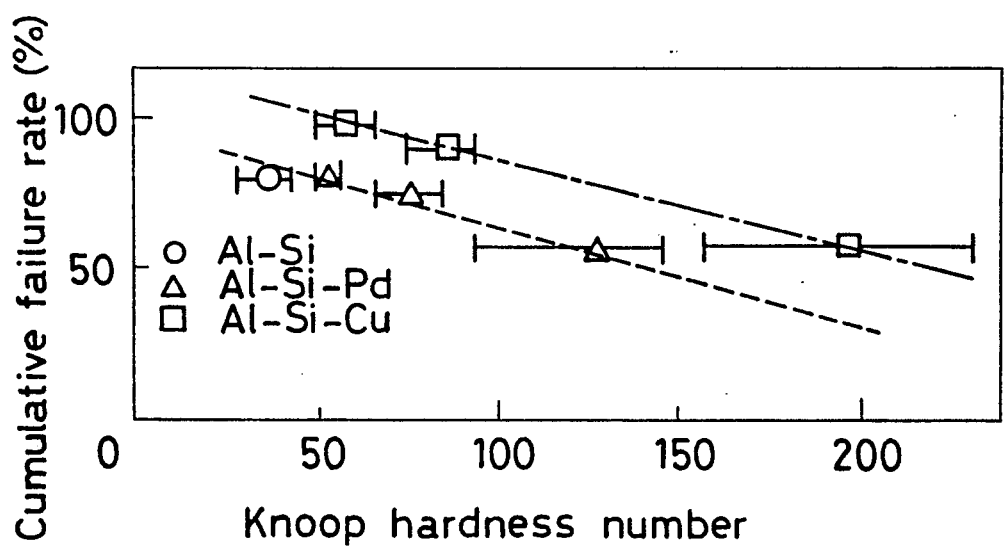
FIG. 3 is a graph showing the relation between hardness and a cumulative failure rate of the metal film according to the present invention.

Next, a stressmigration test is preformed. These aluminum films are patterned on TEG (Test Element Group), and interconnection lines are formed with a width of 0.8 μm. A method of the test is that sample wafers are kept for 2.5 hours at high temperature of 420° C. and open failures of interconnection lines are checked. The relations between the cumulative failure rates and Knoop hardness are shown in FIG. 3. It can be seen from FIG. 3 that Knoop hardness corresponds well to the cumulative failure rates. We can say that the higher the hardness is, the smaller the failure rate is in the same kind of alloy, that is, a harder film has better tolerance of stressmigration.

In addition, it is also found from the results that the stressmigration tolerance of the metal film of the Al-Si-Pd film or the Al-Si-Cu film is superior to that of the Al-Si film.

Then, the thus formed metal films 3, that is, the Al-Si film, the Al-Si-Pd film and the Al-Si-Cu film are patterned and then an SiO$_2$ film having a thickness of 3000 Å is formed thereon as a protective film by the CVD method to form samples. The stressmigration tolerance of each of the metal films having the protective films is evaluated by the conventional evaluating method by aging the samples. As a result, it is confirmed that the stressmigration tolerance of the Al-Si-Pd film or the Al-Si-Cu film is superior to that of the Al-Si film.

II Evaluating Procedure

Procedure for evaluating performance of the aluminum alloy wiring film will be described in detail.

First, a film to be evaluated such as a BPSG film is formed on an Si substrate with a thickness of 1.1 μm.

At this time, as a reference film, an Al-Si-Cu film or the like which has been already used as a metal wiring material is deposited by sputtering on the substrate.

Then, hardness of each of the films is measured. When the hardness of the film to be evaluated is higher than that of the reference film (for example, it is greater than Knoop hardness of 200 (referring to FIG. 2)), a protective film is formed on the film to be evaluated and then evaluated by the conventional aging evaluating method.

When the hardness of the film to be evaluated is smaller than that of the reference film, since the stressmigration tolerance is considered to be inferior, the aging evaluation is not performed.

Thus, since the film to be evaluated is selected before the aging processing, evaluation can be efficiently performed.

In addition, when a degree of the influence of the stressmigration tolerance upon the metal film of the protective film is known or its influence is very small, the stressmigration tolerance of the metal film is evaluated by only comparing the hardness. Thus, the step of forming the protective film and the aging processing can be omitted, whereby time required for the evaluation can be further reduced.

In the above embodiment, the AlSi film, the Al-Si-Pd film, the Al-Si-Cu film are formed by Al-1 wt % Si, Al-1 wt % Si-0.3 wt % Pd, Al-1 wt % Si-0.5 wt % Cu, respectively.

As described above, according to the present invention, it is possible to evaluate the performance of the metal wiring film for a short time using few samples.

While only certain presently preferred embodiments have been described in detail, as will be apparent with those skilled in the art, certain changes and modifications can be made without departing from the scope of the invention as defined by the following claims.

What is claimed is:

1. A method for evaluating performances of an aluminum alloy wiring film comprising the steps of:
    forming a first aluminum alloy film on a first substrate;
    forming a second aluminum alloy film on a second substrate;
    measuring hardness of both of said first and second films;
    comparing the hardness between the first and second films to determine which one is superior; and
    subjecting the film superior in hardness to a test for measuring and evaluating a stressmigration of the film.

2. A method according to claim 1, wherein said reference film and said evaluated film are formed on the substrates by sputtering.

3. A method according to claim 2, wherein each of the substrates has a BPSG film on a surface thereof.

4. A method for evaluating performance of an aluminum alloy wiring film comprising the steps of:
    forming a reference aluminum alloy film having a predetermined thickness on a substrate;
    forming an aluminum alloy film to be evaluated on another substrate with the same thickness as that of the reference film;
    measuring hardness of both of the films;
    forming a protective film on the evaluated alloy film if the hardness of the evaluated film is higher than that of the reference film; and aging said evaluated film to evaluate stressmigration tolerance of the aluminum alloy film having the protective film.

5. A method according to claim 4, wherein said reference film and said evaluated film are formed on the substrates by sputtering.

6. A method according to claim 4, wherein each of the substrates has a BPSG film on a surface thereof.

7. A method for evaluating performance of an aluminum alloy wiring film comprising the steps of:
    forming a first aluminum alloy film on a substrate;
    forming a second aluminum alloy film on another substrate;
    measuring hardness of both of the films; and
    evaluating superiority of stressmigration of the aluminum alloy films by comparison between the films in hardness;
    wherein each of the substrates has a BPSG film on a surface thereof.

8. A method for evaluating performances of aluminum alloy wiring films comprising the steps' of:
    forming a different aluminum alloy film on each of a plurality of substrates;
    measuring hardness of each of the respective films;
    comparing the hardness among the respective films; and
    subjecting the films to stressmigration tests in accordance with their respective order of hardness.

* * * * *